United States Patent [19]
Philipp et al.

[11] Patent Number: 5,952,487
[45] Date of Patent: Sep. 14, 1999

[54] DNA SEQUENCES OF THE PAPILLOMAVIRUS HPV42 FOR USE IN DIAGNOSIS

[75] Inventors: Wolfgang Philipp; Martin Sapp, both of Mainz, Germany; Stewart Cole, Clamart; Nadine Honore, Colombes, both of France

[73] Assignee: Institut Pasteur, Paris, France

[21] Appl. No.: 08/167,854

[22] PCT Filed: Jun. 25, 1992

[86] PCT No.: PCT/FR92/00586

§ 371 Date: Feb. 10, 1994

§ 102(e) Date: Feb. 10, 1994

[87] PCT Pub. No.: WO93/00435

PCT Pub. Date: Jan. 7, 1993

[30] Foreign Application Priority Data

Jun. 28, 1991 [FR] France ................................. 91 08125

[51] Int. Cl.⁶ .............................. C12N 15/37; C07N 21/04
[52] U.S. Cl. .................. 536/23.72; 536/23.1; 536/24.32; 435/69.3

[58] Field of Search ........................ 435/69.3; 536/23.72, 536/23.1, 24.32

[56] References Cited

PUBLICATIONS

Philipp, Wolfgang, et al., "Human Papillomavirus Type 42: New Sequences, Conserved Genome Organization," Virology 186:331–334 (1992).
Bowie et al. Science 247:1306–1310, Mar. 1990.
Kumar et al. PNAS 87:1337–1341, Feb. 1990.
Munger et al. EMBO Journal 8(13):4099–4105 1989.
Beaudenon et al. Virology 161:387–384 1987.

*Primary Examiner*—Anthony C. Caputa
*Assistant Examiner*—Robert C. Hayes
*Attorney, Agent, or Firm*—Finnegan, Henderson, Farabow, Garrett & Dunner, L.L.P.

[57] ABSTRACT

DNA sequences derived from human papillomavirus HPV42 are disclosed. Also disclosed are methods of using these sequences as hybridization probes in diagnostic assays.

9 Claims, 11 Drawing Sheets

```
  +1 CTTATTATAA ACTACAATCC TGGCTTTGAA AAATAAGGGA GTAACCGAAT TCGGTTCAAC
 +61 CGAAACCGGT ACATATATAA ACCACCCAAA GTAGTGGTCC CAGTTAAGGC AGAATGTCAG
+121 GTACATCTGC CTCATCACAG CCACGCACAT TATACCAATT GTGTAAGGAA TTTGGGCTGA
+181 CATTGCGGAA TTTACAGATT TCCTGCATTT GGTGCAAAAA GCACTTAACA GGCGCAGAGG
+241 TGCTCGCGTA CCATTTAAA GATTTGGTAG TGGTGTGGAG GAAGGACTTT CCATATGCTG
+301 CATGTGCATT TTGTTTAGAA TTTAATTCTA AAATTTGTGC ACTGCGACAC TACGAAAGAT
+361 CAGCATTTTG GTATACAGTG GAGAAAGAAA CTGGACTACT TTTAGAAGAA CAACAAATTA
+421 GATGTGCCTT GTGTCAAAAG CCGTTATCAC AGAGCGAAAA AAACCATCAT ATTGATACAG
+481 GTACAAGATT TCAATTTATA TTGTGTCAGT GGACGGGTCG GTGTACGCAT TGCAGAGGAC
+541 AATGCGTGGA GAGACGCCTA CCCTAAAGGA CATTGTTTTG TTTGACATAC CAACGTGTGA
+601 GACACCCATT GACCTGTATT GCTATGAACA ATTGGACAGC TCAGATGAAG ATGACCAAGC
+661 CAAACAGGAC ATACAGCGTT ACAGAATACT GTGTGTGTGT ACACAGTGTT ACAAGTCTGT
+721 TAAACTCGTT GTGCAGTGTA CAGAGGCGGA CATAAGAAAC CTGCAACAGA TGCTTTTGGG
+781 CACACTGGAT ATTGTGTGTC CTTTGTGTGC CCGCGTGGAG TAACTGCAAT GGCGGATGAT
+841 ACAGGTACAG AGGAGGGGCT AGGGTGTTCT GGATGGTTTT GTGTAGAAGC TATAGTAGAC
```

FIG. 1A

```
+901  AAAACAACAG AAAATGCTAT TTCAGATGAC GAGGACGAAA ATGTAGACGA TAGTGGGTTA

+961  GATCTTGTGG ATTTTGTAGA TAATAGTACA GTAATACATA CAAAGCAGGT ACATGCACAA

+1021 GCCTTATTAA ATAAACAACA AGCACATGCA GATCAGGAGG CAGTACAGGC ACTAAAACGA

+1081 AAGCTATTAG GCAGTCCATA TGAAAGCCCT GTCAGTGATT CACAGCACAG CATAGACAAC

+1141 GAACTAAGTC CTAGGCTTGG CGGTTTAACG CTATGTCGGG GGTCCCAAGG GGCCAAACGA

+1201 CGATTATTCC AGTCACTGGA AAATCGAGAC AGTGGATATG GCTATTCTGA AGTGGAAGTA

+1261 CAGCAGACAC AGGTAGAACA CGGACATGGC GCCGTACATG GGACTATGGG TAACGGGGGG

+1321 GCAGTGGGTA GTGAACTTGG GGTGCAGGAA AATGAAGAAG GTAGTACTAC AAGTACGCCT

+1381 ACAACAAGGG TGGTAGAATT ACTTAAGTGT AAGAACCTGC ATGCAACATT GTTAGGTAAG

+1441 TTTAAAGAAT TGTTTGGAGT GTCATTTGGC GATTTAGTAA GACAGTTTAA AAGTGACAAA

+1501 AGCAGTTGTA CAGACTGGGT TATTGCAGCA TTTGGGGTTA ATCATAGTAT TGCAGAAGGG

+1561 TTTAATACAT TAATTAAAGC AGATTCACTA TATACACATA TACAATGGCT AACCTGTACG

+1621 TGGGGCATGG TGTTATTAAT GCTAATTAGA TTTAAATGTG GAAAAAATCG TACTACAGTG

+1681 TCCAAAGGCC TTAGTAAATT ATTAAACATA CCTACAAATC AATTATTAAT AGAGCCACCT

+1741 CGGTTACAAA GTGTGGCTGC CGCCATATAC TGGTTTAGAT CAGGAATATC TAATGCTAGC
```

FIG. 1B

```
+1801 ATTGTAACCG GAGACACACC AGAGTGGATT CAAAGACAAA CAATTTTAGA ACATTGTTTT
+1861 GCAGATGCCC AATTTAATTT AACAGAAATG GTGCAATGGG CATATGATAA TGATATTACT
+1921 GAAGACAGTG ACATTGCATA TGAATATGCA CAACGGGCAG ACAGGGATAG CAATGCTGCT
+1981 GCATTTTTAA AAAGTAACTG CCAGGCAAAA TATGTAAAAG ATTGTGGGCGT CATGTGCAGA
+2041 CATTATAAAA AAGCACAAAT GAGACGTATG TCTATGGGTG CATGGATAAA ACATAGAAGT
+2101 GCCAAGATAG GGGATAGTGG AGATTGGAAA CCTATAGTAA AATTATTAG ATATCAACAA
+2161 ATTGATTTTT TAGCATTTAT GTCTGCATTT AAAAAGTTTT TACATAATAT ACCTAAAAAA
+2221 AGTTGTTTAG TGTTAATTGG TCCTCCAAAT ACAGGAAAAT CACAGTTTGG AATGAGTTTA
+2281 ATAAACTTCT TAGCAGGAAC TGTAATATCA TTTGTAAATT CACATAGCCA TTTTTGGCTG
+2341 CAGCCATTGG ACAGTGCAAA AATAGCTATG CTGGATGATG CAACTCCACC ATGTTGGACA
+2401 TATTTAGATA TATATTTAAG AAATTTATTA GATGGCAATC CATGCAGTAT AGATAGAAAA
+2461 CATAAAGCAT TAACAGTTGT TAAGTGCCCA CCATTACTTA TAACATCAAA TACAGATATT
+2521 AGAACAAATG ACAAAATGGAA ATACCTATAC AGCAGAGTTA GTTTATTGA ATTTCCAAAT
+2581 CCATTTCCAT TAGATACAAA TGGAAATCCT GTATATGAAT TAAATGACAA AAATTGGAAA
+2641 TCATTTTTTC AAAGGTTGTG GTCCAGCTTA GAATTTCAAG AATCAGAGGA CGAGGAAGAC
```

FIG. 1C

```
+2701  TATGGAGAGA  CTGGCCAAAC  GTTTAGATGC  GTGCCAGGAA  CAGTTGTTAG  AACTGTATGA
+2761  GGAAAATAGT  AGGGATTTAC  AAAAACATAT  TGAACATTGG  AAATGTTTAC  GTATGGAGGC
+2821  AGTGGTATTG  TATAAGGCCC  GTGAAATGGG  CTTTGCAAAT  ATAGGACATC  AAATAGTACC
+2881  AACATTGGAA  ACATGTAGAG  CCAAGGCCCA  CATGGCAATT  GAAATACACT  TGGCATTAGA
+2941  GACATTATTG  CAGTCCTCGT  ATGGTAAAGA  ACCATGGACA  TTGCAAGAAA  CAAGTAATGA
+3001  ACTGTGGCTT  ACGAATCCTA  AAAAATGTTT  TAAAAAACAA  GGACGTACCG  TGGAGGTTAT
+3061  ATTTGATGGA  AAACAGGACA  ATGCAATGCA  TTATACAGCA  TGGACATATA  TATATATACA
+3121  AACTGTGCAA  GGTACATGGT  GTAAAGTACA  AGGACACGTT  TGCCATGCAG  GACTATATTA
+3181  TATTGTGGAA  AATATGAAAC  AGTTTTATTG  TAATTTTAAA  GAGGAGGCAA  AAAAATATGG
+3241  GGTAACAGAC  CAATGGGAGG  TACATGATGG  CAATCAGGTG  ATTGTTTCTC  CTGCACCCAT
+3301  ATCTAGCACC  ACATCCACCG  ACGCAGAGAT  ACCCTCTACT  GGATCTACTA  AGTTGGTACA
+3361  ACAAGTGTGC  ACCACAAACC  CATTGCACAC  CACAACGTCC  ATTGACAACC  ACCACGCAGA
+3421  CTGTACAGAC  GGAACAGCAT  ACAACGTGCC  CATCCAAACC  TCACCGCCAC  GAAAACGATA
+3481  CAGACAGTGT  GGACAGTCGC  CATCACAGCA  CCTGCAGCAC  TCAAACCCCA  GCATCCCCAG
+3541  CATCCCCAGC  GCATCCGTGG  ACCCTGGATT  GTGTGGGGTC  AGAACTAACA  GTGAAAACTG
```

FIG. 1D

+3601 TAACAAGCGA CGGAACCACT GTGGAAGTCA GGCTACGCCT GTAATTCATT TACAAGGTGA

+3661 CCCTAATTGC CTAAAATGCC TACGATTTAG GCTAAAAAGA AATTGTTCAC ATTTATTTAC

+3721 ACAGGTGTCA TCTACATGGC ATTTAACAGA AAATGATTGT ACACGTGACA CTAAAACTGG

+3781 TATAATAACA ATACATTATT ATGATGAAGC ACAAAGAAAT TTATTTTAA ATACTGTAAA

+3841 AATACCTTCT GGGATAAAAT CCTGTATTGG ATATATGTCT ATGTTACAGT TTATATGATT

+3901 AGTTGTATAT GTGTATAAAC AGTTATAGGA CTTCAATACT GTGACTCCAC AACGTGTGGG

+3961 ACAACCGGCC AGAAACTGCT GCTTTTATTG TTTATAGTTG TTGGTGCGTG TGTTGTGTGT

+4021 GTGTGGATTA GTTACAAAA TTATCCATAT CCTGTATGGG CCTCTTGCCT TGCTAGCTAC

+4081 CTAACATTGG TGCTATTATC ATGGTTGCAG GTACTAACAT ACTTTGACTA TTTTTTCTA

+4141 TGTTTAATCA TTCTTGGTAT TCCTTCTGTC TTACTAACAT TACTAATACA TTTAGCAATA

+4201 CAATAACACA TATTAGTTTA GGTGTGTGTG TGTGGTGTGC ATGTGATTTG TACATGGTTG

+4261 TACATATATA ATACCAATTA TTGTTTGGCT ACTATTTTCA TTTATAGCCA CACTGCTGTT

+4321 TTGCATATTG GTATTACAAA CATATAAACT GTTACCATAC GTATATACAG TGCTGTAAAT

+4381 AAACTTTTGT TATATTGTGT GTACTTCTTT TGTGCTATTA CAATGCCACC ACAACGGTCC

+4441 CGCAGACGAA AGCGGGGCCTC TGCCACACAA TTATATCAAA CGTGTAAGGC CTCAGGACA

FIG. 1E

```
+4501  TGTCCTCCAG ATGTTATTCC CAAAGTTGAA GGAACCACAT TGGCAGATAA AATTTACAA
+4561  TGGGGTAGTT TAGGCGTGTT TTTTGGGGGG TTGGGAATTG GCACTGGTGC AGGTACGGGT
+4621  GGGCGCACGG GCTATGTGCC TCTGGGAACA AGGCCTCCTG TAATTGCTGA ACCAGGACCT
+4681  GCAGTACGCC CACCAATAGC TGTTGACACC GTGGGGCCAT CTGATCCTTC TATTGTTTCC
+4741  TTATTAGAAG AGTCATCAGT TATTGATGCA GGAATAACAG TACCTGATAT TACTTCTCAT
+4801  GGAGGTTTTA ATATTACTAC CCACTAATAC ATCTACTGGT GGGCCTGCCT CAACGCCTGC TATATTAGAT
+4861  ATCTCCCCTC CCACTAATAC TATACGTGTC ACAACAACTA CATCTACCAA TCCTTTATAT
+4921  ATTGATCCTT TTACATTGCA GCCGCCATTG CCAGCAGAGG TTAATGGGCG CCTATTAATA
+4981  TCTACTCCTA CCATCACACC CCACTCATAT GAAGAAATAC CAATGGACAC GTTTGTTGTA
+5041  TCTACAGATA CAACTAACAC ATTTACTAGT ACTCCCATTC CTGGCCCTCG GTCGTCTGCA
+5101  CGCCTGGGGT TATATTCTAG AGCAACGCAA CAACGTCCAG TTACTACCAG TGCATTTTA
+5161  ACATCTCCTG CACGGTTGGT TACTTATGAC AATCCAGCCT ATGAAGGACT TACGGAGGAT
+5221  ACATTAGTAT TTGAACATCC ATCCATTCAT ACTGCACCTG ACCCTGATTT CATGATATA
+5281  GTTGCATTGC ATCGTCCTAT GTTATCATCC AAACAGGGTA GTGTACGTGT TAGTAGAATT
+5341  GGACAAAGGC TGTCTATGCA GACACGTCGC GGGACCCGTT TTGGGTCACG TGTACACTTT
```

FIG. 1F

```
+5401  TTTCATGACC TTAGCCCTAT TACACACTCT TCAGAAAACTA TTGAATTACA GCCTTTATCT

+5461  GCTTCTTCAG TATCTGCAGC CTCCAATATT AATGATGGGT TATTTGATAT TTATGTTGAT

+5521  ACTAGTGATG TAAATGTTAC AAATACCACT TCCTCTATAC CTATGCATGG TTTTGCTACC

+5581  CCCGTTTGT CCACTACATC TTTCCCTACA TTACCTAGCA TGTCTACACA TTCTGCCAAT

+5641  ACCACCATAC CTTTTTCGTT TCCTGCCACT GTGCATGTGG GCCCTGATTT ATCTGTGTG

+5701  GACCACCCAT GGGACAGTAC CCCAACGTCT GTAATGCCTC AGGGTAACTT TGTAATGGTA

+5761  TCAGGATGGG ATTTTATATT GCATCCTAGT TATTTTTGGC GTAGGCGCCG TAAACCTGTA

+5821  CCATATTTTT TTGCAGATGT CCGTGTGGCG GCCTAGTGAC AACAAGGTTT ATCTACCTCC

+5881  TCCTCCTGTT TCCAAGGTGG TCAGCACTGA TGAATATGTG CAACGCACCA ACTACTTTTA

+5941  CCATGCCAGC AGTTCTAGGC TATTGGTTGT TGGTCACCCT TATTACTCTA TTACAAAAAG

+6001  GCCAAATAAG ACATCTATCC CCAAAGTGTC TGGTTTACAG TACAGAGTAT TTAGAGTTAG

+6061  GCTCCCTGAT CCTAATAAGT TTACATTGCC TGAAACTAAT TTATATAACC CAGAGACACA

+6121  GCGCATGGTG TGGGCCTGTG TGGGGCTAGA AGTAGGTCGT GGACAGCCTT TGGGCGTTGG

+6181  TATTAGTGGC CATCCATTAT TGAATAAGTT GGATGATACT GAAAATGCGC CTACATATGG

+6241  TGGAGGCCCT GGTACAGACA ATAGGGAAAA TGTTTCTATG GATTATAAAC AAACACAGTT
```

FIG. 1G

```
+6301  GTGTTTAGTT  GGCTGTAAAC  CTGCCATAGG  GGAGCACTGG  GGTAAAGGTA  CTGCCTGTAC

+6361  ACCACAGTCC  AATGGTGACT  GCCCACCATT  AGAATTAAAA  AATAGTTTTA  TTCAGGATGG

+6421  GGATATGGTG  GATGTAGGGT  TTGGGGCACT  AGATTTGGT   GCTTTACAAT  CCTCCAAAGC

+6481  TGAGGTACCT  TTGGATATTG  TAAATTCAAT  TACTAAATAT  CCTGATTACT  TAAAAATGTC

+6541  TGCTGAGGCC  TATGGTGACA  GTATGTTTTT  CTTTTTAAGG  CGAGAACAAA  TGTTTGTTCG

+6601  TCATTTGTTT  AATAGGGCTG  GCGCAATTGG  TGAACCTGTA  CCTGATGAAC  TGTATACCAA

+6661  GGCTGCTAAT  AATGCATCTG  GCAGACATAA  TTTAGGTAGT  AGTATTTATT  ATCCTACCCC

+6721  TAGTGGTTCT  ATGGTAACAT  CTGATGCACA  ACTATTTAAT  AAACCATATT  GGTTACAACA

+6781  AGCACAAGGA  CACAATAATG  GTATATGTTG  GGGAAATCAG  CTATTTTTAA  CTGTGGTTGA

+6841  TACTACCCGT  AGTACTAACA  TGACTTTGTG  TGCCACTGCA  ACATCTGGTG  ATACATATAC

+6901  AGCTGCTAAT  TTTAAGGAAT  ATTTAAGACA  TGCTGAAGAA  TATGATGTGC  AATTTATATT

+6961  TCAATTGTGT  AAAATAAACAT TAACTGTTGA  AGTTATGTCA  TATATACACA  ATATGAATCC

+7021  TAACATATTA  GAGGAGTGGA  ATGTTGGTGT  TGCACCACCA  CCTTCAGGAA  CTTTAGAAGA

+7081  TAGTTATAGG  TATGTACAAT  CAGAAGCTAT  TCGCTGTCAG  GCTAAGGTAA  CAACGCCAGA

+7141  AAAAAAGGAT  CCTTATTCAG  ACTTTTGGTT  TGGGAGGTA   AATTTATCTG  AAAAGTTTTC
```

FIG. 1H

```
+7201  TACTGATTTA GATCAATTTC CTTTAGGTAG AAAGTTTTTA CTGCAGGCCG GGTTGCGTGC

+7261  AAGGCCTAAA CTGTCTGTAG GTAAACGAAA GGCGTCTACA GCTAAATCTG TTTCTTCAGC

+7321  TAAACGTAAG AAAACACACA AATAGATGTA TGTAGTAATG TTATGATACA TATTTATGTT

+7381  ATTTATTTGT GTACTGTGTT AATAAACTAC TTTTTATATG TTGTGTGTTC TCCATTTGT

+7441  TTTTTGTACT CCATTTTGTT TCTAGACCGA TTTCGGTTGT ATCTGGCCTG TTACCAGGTG

+7501  CATTGGCCAT GTTCCCTAAC ATTTTGCAAA CCTATTCACT TTTTAAATTT ATAAATGCAA

+7561  TATGTGCTGC CAACTGTTTT ATGGCACGTA TGTTCTGCCA ACGTACACTC CCTAATTCCT

+7621  TTACATAACA CACACGCCCT TGCACAGGCA TGTGCACAAA GGTTGGCAAA GGTTAGCATA

+7681  TCTCTGCAGT TACCCATTTC CTTTTTCCTT TTTTTTATGT ATGAGTAACT TAATTGTTAT

+7741  ATGTAATAAA AAAGTTTTA GGCACATATT TTCAGTGTTG GCATACACAT TTACAAGTTA

+7801  CCTTGGCTTA AACAAGTAAA GTTATTTGTC ACTGTTGACA CATTACTCAT ATATATAATT

+7861  TGTTTTTAAC ATGCAGGTGG CAACCGAAAC CGGTACATAA ATCCTTCTTA TTCTTTT
```

(SEQ ID NO: 1)

FIG. 1I

DNA SEQUENCES OF THE PAPILLOMAVIRUS HPV42 FOR USE IN DIAGNOSIS

This is the National Phase of PCT/FR 92/00586, filed Jun. 25, 1992.

BACKGROUND OF THE INVENTION

The invention relates to specific DNA sequences derived from the genome of papillomavirus HPV42, including the sequence corresponding to its entire genome, as well as recombinant DNAs, in particular vectors containing all or part of those DNA sequences which code for structural proteins of these papillomaviruses or parts of these proteins. The invention also relates to the cell cultures transformed by the said recombinant DNAs under conditions optionally enabling them to express the corresponding sequences derived from the HPV42 genome in the form of the corresponding proteins. Finally, the invention relates to diagnostic kits making use of some of the products defined above or those whose description follows and their novel uses, more particularly for the discrimination between benign genital epithelial lesions and lesions of the carcinoma or precarcinoma type induced by papillomaviruses.

Most of the 60 or more different types of human papillomaviruses hitherto identified are all epitheliotropic viruses presumed to be responsible for the induction of an abnormal growth of the infected tissue (1, 39). Depending on their tissue specificities and respective predominance in benign or malignant tumors, the types of human papillomaviruses (HPV) have been classed in different groups, for example low risk groups (HPV 6, 11) (2, 3), high-risk groups (HPV 16, 18, 31, 33, 39, 57) (1, 4–8), genital HPVs and HPVs associated with epidermodysplasia verruciformis (HPV 5, 8, 19, 25, 47) (1, 9–11), etc. . With the objective of gaining a better understanding of their mutual relationship and, if necessary, of revealing the nature of their tissue specificities, it has also been suggested that sequence comparisons be made. However, attempts to establish correlations between certain characteristics of the virus and certain specific characteristics of their respective genomes have not really proved to be successful up to now. The demonstration of the difficulty of establishing such correlations is illustrated particularly by the result of the sequence studies which have been conducted on papillomavirus HPV42, which had already been isolated from vulvar papillomas, by the use of a DNA of the oral HPV32 type (12) as probe under conditions of low stringency (13). According to this last publication HPV42 proved to be present in 3.5% of the genital lesions which in most cases exhibited histological characteristics of condylomas or flat papillomas.

SUMMARY OF THE INVENTION

The invention is also based on the discovery of specific sequences present in HPV42, sequences which form the basis of its originality and which allow particularly discriminating detections of papillomaviruses of the HPV42 type and confirmation (or refutation) of results of in vitro diagnoses performed with probes containing DNA sequences derived from other papillomaviruses. These sequences or fragments of these sequences can also be used to constitute particularly sensitive hybridization probes, in particular primers which make possible analyses by the so-called PCR method.

In what follows use will be made of some abbreviations derived from English expressions. They are conserved in the text to facilitate the reading of the text by specialists who are used to these abbreviations.

They are given below, and are followed by the complete English: expressions from which they derive NCR: non coding region ORF: open reading frame PVF: papillomavirus-enhancer associated factor GRE: consensus glucocorticoid responsive element bp: base pairs PCR: polymerase chain reaction nt: nucleotide Before proceeding further with the description of these sequences or sequence fragments, it is proposed to make a brief review of the state of the prior art and then to provide a detailed description of the HPV42 genome.

BRIEF DESCRIPTION OF THE DRAWINGS

The remainder of the description will be given with reference to the appended figures, the legends to which are the following:

FIG. 1: 1(*a*), 1(*b*), 1(*c*), 1(*d*), 1(*e*), 1(*f*), 1(*g*), 1(*h*), 1(*i*) (SEQ ID NO: 1: Nucleotide sequence of the DNA strand of HPV42 analogous to the mRNA. Position 1 on the circular genome was determined by alignment with positions 1 of HPV11 and HPV39.

First nucleotides: +1, +1801, +3601 and +7201.

Figure 2:
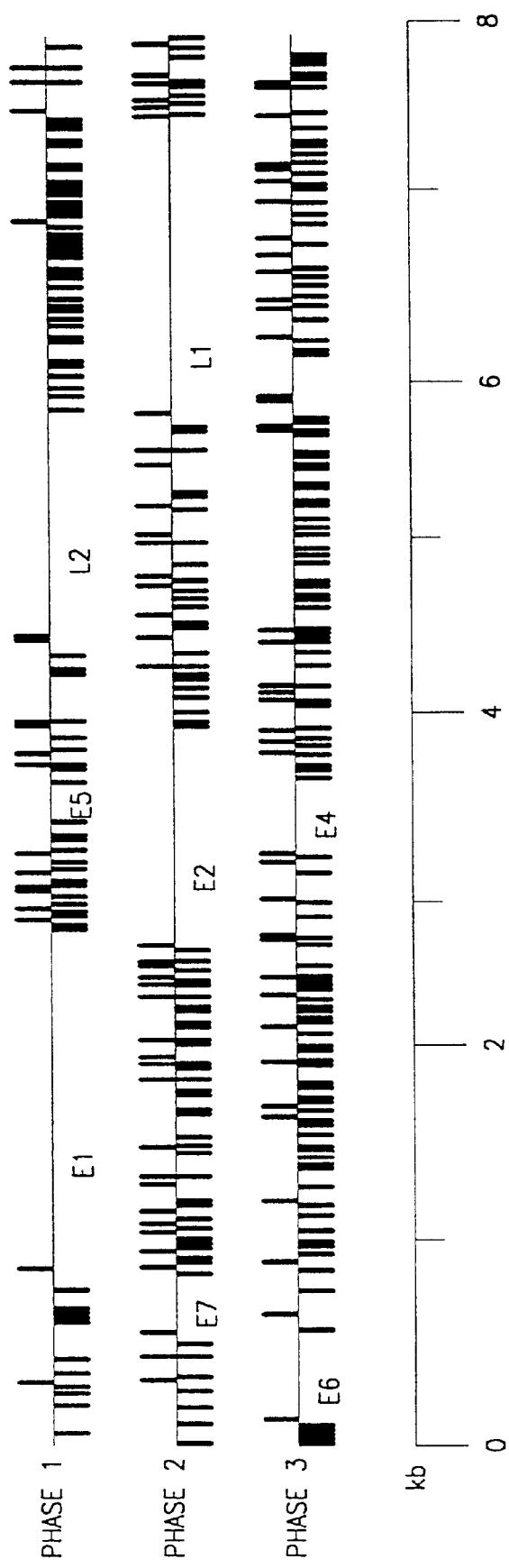

FIG. 2: Distribution of the start codons (bars above) and stop codons (bars below) in the mRNA for the three reading frames of the HPV42 DNA. The ORFs were identified by comparison with other types of HPV. The numbering is consistent with that of FIG. 1.

Figure 3:
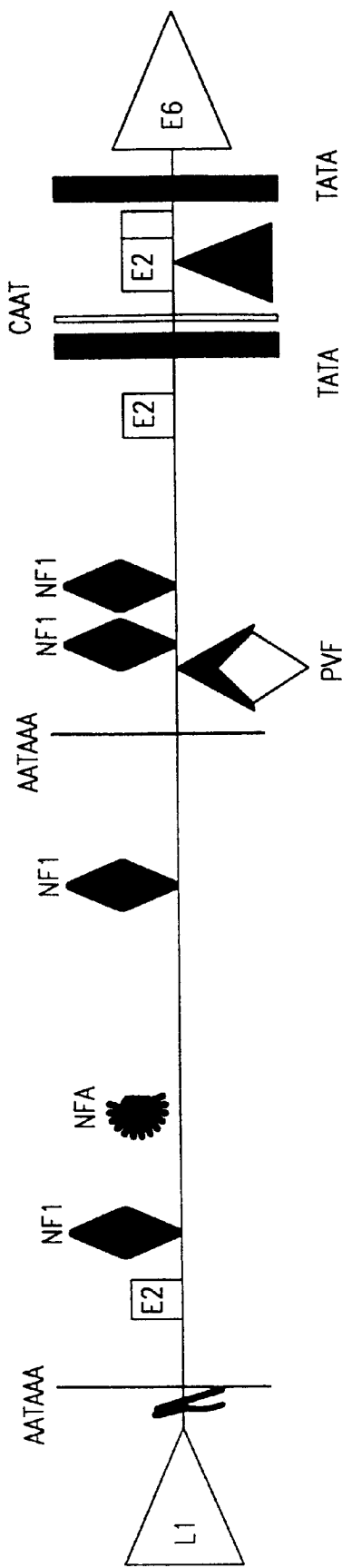

FIG. 3: Principal characteristics of the non-coding region (NCR). The following sequence motifs of the NCR extending from nucleotide 7346 to nucleotide 113 (nt. 7346–113) are shown. Certain elements are specified below, in particular palindromes of 12 bp specific for the papillomavirus (nt.7466, 7883, 44, 59); polyadenylation site: nt.7401; TATA box: nt.6.74; CAAT box: nt. 15; conserved promoter element (AAAGGGAGTA): nt.34; nuclear factor 1 binding site (NF1): nt. 7503, 7663, 7778, 7803. binding sites for the factor associated (NFA) with the (NF1) factor: nt. 7552; binding site for the factor associated with the papillomavirus-enhancer (PVF) (nt. 7760).

DESCRIPTION OF THE PREFERRED EMBODIMENTS

The HPV42 genome, propagated in plasmid pSP64 was subcloned by "shotgun" fragmentation in phage M13 and sequenced by the dideoxy chain termination method (14). Parts corresponding to 93% of the entire genome were obtained from each of the strands and each of the nucleotides was sequenced five times. The regions for which doubt still remained were sequenced again in both directions by using synthetic oligonucleotides as primers in both directions. The long sequence of 7917 bp (FIG. 1) (SEQ ID NO: 1) has a GC content of 39.5%. The nucleotide +1 was defined by alignment of the sequence with those of the HPVs of types 11 and 39. The restriction map already published (13) was confirmed, with the exception of two additional AccI sites at positions 895 and 943, on either side of a BglII site.

The analysis of the sequences corresponding to the open reading frames (ORFs) has revealed the conservation of the organization that is found in all of the HPV genomes (FIGS. 2) (15, 39). All of the ORFs are localized on the same DNA strand. The E4 region is included completely in the E2 region, whereas the E1 as well as the L1 and L2 regions are partially superposed. Neither E4 nor E5 possesses a start ATG codon (FIG. 1; Table 1). Six polyadenylation signals (AATAAA) were localized in the genome. Two of them (nt.4378, 7401) consist of a series of adjoining thymidines and purines and a dinucleotide CA (16, 17) is located downstream from the early and late gene clusters, respectively. All are probably used for polyadenylation. A non-coding region (NCR) of about 680 bp is located between the stop codon of LI and the initiation codon of E6.

The general characteristics of the NCRs of all of the HPVs are well conserved in HPV42 (FIG. 3). Four copies of the amplification motif ACCGNNNNCGGT (SEQ ID NO: 2) remain placed under the dependence of E2 (nt.444, 59, 7466, 7883) (18, 19), binding sites for the NF1 transcription factors (nt.7503, 7663, 7778, 7803) (21, 22), NFA (nt.7552) (20), a papillomavirus amplification protein (NFA; nt. 7760) (20), two TATA boxes (nt.6, 74), a putative CAAT box (nt.15) as well as a conserved promoter element AAAGG-GAGTA (nt. 34) (23) are situated in the NCR. No consensus element obviously interacting with a glucocorticoid (GRE) has been located in the NCR (18, 19, 24). As in HPV39, the presence is noted of a GRE comprising 3 "mismatches" in the ORF of LI (nt.6555) (8) in HPV42.

The proteins E6 and E7 of the HPV associated with malignant tumors have been recognized as playing a crucial role in the transformation of the cells (25–28). The Cys-X-X-Cys motifs which exhibit the form of "zinc fingers" (29, 30) the role of which has been judged essential for transformation in the case of HPV16 (31), are present 4 times in E6 and twice in E7. Potential donor (nt.237) and acceptor (nt.412) splicing sites in the ORF of E6 capable of being transcribed into an mRNA coding for a spliced E7 protein, E6*, are well conserved in HPV42 (32–34). Up to now the splicing site had only been identified in HPVs associated with anal-genital cancers (6). In addition, the cell division motif of protein E7, which had been associated with its transformation capacity (31, 35–37), is completely conserved in HPV42.

No pronounced sequence homology with other types of HPV whose sequences are known could be detected. In a computer-assisted analysis of the homologies, homologies of the order of 52 to 56% were obtained with the HPVs of type 6b, 11, 16, 18, 31 and 33. These values are very low when they are compared with sequence homologies which can be observed between viruses of the same sub-group (4–11). In addition HPV42, which is associated with benign genital lesions, exhibits characteristics which are presently known only for HPVs associated only with carcinomas; the same holds for the presence of a E6* site and the cell division motif conserved in protein E7. In addition, a GRE present in the NCRs of all of the genital HPVs sequenced up to now (8) is, on the other hand, absent from the NCR of HPV42. HPV42 may thus be considered to be the first representative of a novel group of human papillomaviruses to be sequenced.

Hence, it follows from the foregoing that the organization of the genome is conserved in the case of HPV42 as it is for all of the HPVs. Inspite of its association with benign genital lesions, HPV42 exhibits characteristics which have been found up to now only either in HPVs associated with invasive carcinomas or in non-genital HPVs. In addition, no extensive sequence homology is observed with the known HPVs. The nucleotide sequence provided by the invention thus testifies to the identification of the sequence of the first type of a novel subgroup of human papillomaviruses.

In a general manner, the invention thus also relates to any recombinant DNA containing the above-mentioned HPV-DNA or fragments of this HPV-DNA, in particular hybridization probes formed from these recombinant DNAs and specially adapted to the detection of an infection by HPV42 or a variant or subtype of this papillomavirus. These probes may either be labelled themselves or be modified at certain nucleotides, in particular with a view to their direct or indirect coupling to a distinct marker. It will be obvious that in these probes the parts foreign to the nucleotide sequence corresponding to the papillomavirus DNA and normally derived from a cloning vector are such that there is no risk of their hybridizing under stringent conditions with the other nucleic acids possibly contained in the sample tested for its possible content of the corresponding papillomavirus DNA or one of its variants.

The procedure according to the invention for the in vitro diagnosis, performed on a biological sample to be tested usually obtained from a human patient, of an infection by a papillomavirus which may lead or have led to a genital neoplasia, in particular a cervical, vulvar or penile cancer, is thus characterized by the placing of such a probe as defined above in contact with the nucleic acids of this sample, where necessary previously made accessible to the probe, preferably under stringent conditions of hybridization, and by the detection of the hybrid formed between the viral DNA under investigation and possibly present in the sample and the said probe.

Each of the probes according to the invention or mixtures containing the above-mentioned probe may be used, in particular, as follows, it being naturally understood that the diagnostic assays described should not be considered as limiting the conditions of use under which these probes or mixtures of probes may in fact be used.

In the example considered, it is required to identify, for example, a HPV of the same type as HPV42 in a biopsy in cells obtained by grattage of the lesions or in biopsy sections fixed by the Carnoy mixture (ethanol chloroform: acetic acid:: 6:3:1) and embedded in paraffin. The examination requires the prior extraction of the DNA from the samples according to known methods and involves the analysis of this DNA by molecular hybridization experiments performed under stringent or less stringent conditions with the aid of radioactive probes (labelled with $^{32}$P or $^{35}$S) prepared from the HPV according to the invention or from mixtures of DNAs or HPVs containing it.

Several hybridization methods may be used. It is possible, for example, to use the dot blot hybridization method. This method comprises, after denaturation of the DNA, the deposition of an aliquot of DNA on membranes (nitrocellulose or "Genescreenplus"), the hybridization of each membrane under the usual conditions with a mixture of probes and the detection of the radioactive hybrids by exposure of the membranes to contact with a radiographic film. It is also possible to use a replica hybridization method. This method comprises the electrophoretic separation on an agarose gel of the DNA fragments obtained after treatment of the DNA by restriction enzymes, the transfer of the fragments to membranes (nitrocellulose or "Genescreenplus") after alkaline denaturation and their hybridization under the usual conditions with the appropriate mixture of probes. The formation of radioactive hybrids is detected after exposure of the membranes to contact with a radiographic film.

The radioactive probes are constituted either by HPV-DNAs labelled by the "nick-translation" method, or by RNAs prepared by transcription of viral DNAs inserted into a vector for example of the SP6 type. The use of radioactive probes offers the advantage of high sensitivity but that does not exclude the use of non-radioactive probes, for example biotinylated probes capable of being recognized by antibodies which are either labelled themselves or are themselves recognized by antibodies bearing an enzymatic, fluorescent etc . . . label.

The invention also relates to competent cell cultures transformed with recombinant DNAs of the type indicated above, in particular those in which the nucleotide sequence corresponding to the DNA or the DNA sequence of HPV39 is placed under the control of transcription and/or regulatory elements for this nucleotide sequence in the said cell culture.

Furthermore and in view of the newly discovered characteristics of HPV42, its use to confirm—or invalidate—an in vitro diagnosis of potential or already existing carcinoma deriving from the use—in particular under the conditions pointed out above—of probes involving HPVs exhibiting characteristics which are similar to those of HPV42, in particular with respect to the ORFs of E6, E6* and/or E7. More particularly, it concerns one or more of the following HPVs: HPV6, HPV 11, HPV16, HPV18, HPV31, HPV33, HPV39 and HPV57.

The invention thus relates more particularly to in vitro diagnostic kits containing:

on the one hand, a probe containing a DNA corresponding to all or part of the HPV42 DNA or of a DNA hybridizing with the former under stringent conditions;

on the other hand, at least one probe containing a DNA corresponding to all or part of the DNA of at least one of the papillomaviruses HPV6, HPV1, HPV16, HPV18, HPV31, HPV33, HPV39 and HPY57.

It will be clearly apparent to the specialist that the performance of the hybridization assays under the conditions which will be given again below (in particular under stringent hybridization conditions) with these sets of probes will enable the specialist either to confirm or at least to qualify a diagnosis of existing or potential carcinoma, or even disprove such a diagnosis. In particular, it would be possible to confirm the diagnosis of existing or potential carcinoma if, for instance, the absence of hybridization of the papillomavirus DNA contained in the sample with HPV42 DNA was observed but a positive response was noted in the hybridization assays with one or other of the DNAs of the kit. On the other hand, a positive hybridization with the HPV42-DNA would also make it possible, depending on the case, either to qualify or to refute a pessimistic diagnosis of this type. In order to obtain a more clear-cut diagnosis, it may be necessary to supplement the hybridization assays with probes containing more specific fragments derived from the HPV42-DNA, more particularly fragments containing all or part of the fragments which, for example, extend between the end nucleotides indicated below respectively: nt. 7342 to nt.870.

Among these fragments preference should often be given to those which contain more particularly all or part of the ORFs E6* or E7 or even all or part of the NCR lacking a GRE site and which extends from nt.7342 to nt.108, in particular from nt.7556 to nt.7576.

The invention also relates to sequences of at least 15 nucleotides derived from the total sequence of HPV42, even sequences from 20 to 40 nucleotides which can be used as primers for PCR and which enable discriminating identification analyses of a papillomavirus to be made by comparison with nucleotide sequences characteristic of papillomaviruses. Preferred primers are derived from nucleotide sequences which were identified above. These primers exist in a double-stranded or single-stranded form.

In keeping with the foregoing, the invention thus relates to a procedure for the in vitro detection of the presence of either a nucleic acid coding for HPV42 or an mRNA comprising in particular the following steps:

a) the placing of the biological sample suspected to contain a DNA related to HPV42, made accessible beforehand to a first primer under conditions allowing the hybridization between this primer and the DNA being sought, in the presence of nucleoside triphosphates and an agent for inducing polymerization (polymerase or reverse transcriptase, depending on the case) and the polymerization starting from these primers hybridized to the mRNA or cDNA in order to produce a duplex formed between the elongation product of the primer hybridized either with the the nucleic acid strand under investigation or with the corresponding mRNA when they are present in the biological sample, b) the denaturation of the duplex obtained at step a) so as to "separate" the elongation product of the primer from the DNA or mRNA to be detected, c) the placing of the elongation product obtained in contact with the second primer (in the sense given to this expression above) which has a nucleotide sequence which (1) is not complementary to that of the first primer and (2) is complementary to a sequence of the elongation product previously formed, d) optional repetition of the steps a), b) and c) in the presence of the first and second primers used in excess and reagents necessary for the production of further elongation products used in turn as matrix for additional syntheses until a sufficient quantity is obtained for the elongation products of the primers used to be detected.

e) the detection of the presence of the elongation products characteristic of the presence of HPV42-DNA or of the corresponding RNA.

The above detection procedure is carried out starting from a biological sample obtained from a patient and consisting of, for example, a biopsy, a surgical sample or a biological fluid.

For more technical details relating to the detection procedure described above or in order to develop variants of this procedure, the person skilled in the art will find it useful to refer to the principles described in the patents US.4.683.202 and US.4.683.195.

Irrespective of the PCR procedure or, more generally, the analytical method based on amplification of gene sequences derived from HPV42 used, it should be understood that the longer the chains obtained after polymerization, the closer the identity of the papillomavirus detected, at least in the region concerned, will be to the HPV42 region from which the probes are derived.

The tables which follow also provide analytical elements relating to the principal characteristics of the HPV42 genome, the results of a comparative analysis (percentages of sequence homologies between HPV42 and the genomes of other papillomaviruses).

Finally, the list of the publications to which reference is made in the present text is provided at the end of this description.

TABLE 1

PRINCIPAL PROPERTIES OF THE GENOME OF HPV42

| ORF | FIRST NUCLEOTIDE | FIRST ATG | NUCLEOTIDE PRECEDING THE STOP CODON | ORF SIZE (bp) | ESTIMATED MOLECULAR WEIGHT (kD) |
|---|---|---|---|---|---|
| E6 | 108 | 114 | 563 | 450 | 17.5 |
| E7 | 476 | 542 | 820 | 279 | 10.7 |
| E1 | 724 | 829 | 2757 | 1929 | 72 |
| E2 | 2672 | 2702 | 3895 | 1194 | 45.2 |
| E4 | 3282 | — | 3641 | 360 | 13.4 |
| E5 | 3919 | — | 4203 | 285 | 10.6 |
| L2 | 4348 | 4423 | 5853 | 1431 | 51.2 |
| L1 | 5756 | 5837 | 7342 | 1506 | 56.1 |

FROM THE FIRST ATG, WITH THE EXCEPTION OF E4 AND E5

TABLE 2

COMPARATIVE ANALYSIS OF THE HPV GENOMES

|  | HPV1 | HPV6 | HPV8 | HPV11 | HPV16 | HPV18 | HPV31 | HPV33 |
|---|---|---|---|---|---|---|---|---|
| DNA[a] | n.t | 56 | n.t | 54 | 55 | 52 | 52 | 53 |
| E6[b] | 30.7 | 48.4 | 27.1 | 49.0 | 41.3 | 39.4 | 40.6 | 41.3 |
| E7[b] | 44.1 | 60.3 | 35.5 | 59.6 | 55.9 | 49.5 | 61.3 | 60.2 |
| E1[b] | 43.1 | 63.8 | 42.8 | 60.7 | 44.3 | 57.7 | 53.7 | 55.2 |
| E2[b] | 32.5 | 46.3 | 36.0 | 50.0 | 35.5 | 42.0 | 30.3 | 43.8 |
| E4[b] | 31.8 | 32.6 | 17.0 | 32.0 | 36.2 | 33.3 | 31.7 | 37.9 |
| E5[b] | n.t. | 20.7 | n.t. | 24.8 | 34.3 | 30.7 | 35.1 | 28.3 |
| L2[b] | 42.1 | 56.4 | 46.3 | 56.8 | 59.7 | 47.2 | 48.0 | 58.3 |
| L1[b] | 53.2 | 69.5 | 49.6 | 68.9 | 73.3 | 63.7 | 74.3 | 71.3 |

THE VALUES REPRESENT PERCENTAGES OF HOMOLOGY AFTER ALIGNMENT WITH THE NEEDLEMAN AND WUNSCH (38) PROGRAM
n.t.: NOT TESTED
[a]: % HOMOLOGY OF NUCLEOTIDES
[b]: % HOMOLOGY OF THE AMINO ACIDS

REFERENCES 1 de Villiers, E. J. Virol. 63, 4898–4903 (1989).
2. Schwarz, E., Dürst. M., Demankowski C., Latterman, O., Zech, R., Wolfsperger, E., Suhai, S. and zur Hausen, H., EMBO J. 2, 2341–2348 (1983).
3. Dartmann, K., Schwarz, E., Gissmann, L. and zur Hausen, H., Virology 151, 124–130 (1986).
4. Seedorf K., Krämer. G., Dürst, M., Suhai, S. and R öwekamp. W. G., Virology 145, 181–185 (1985).
5. Cole, S. T. and Danos, O. J., J. Mol. Biol. 193, 599–608 (1987).
6. Goldsborough, M. D., DiSilvestre, D., Temple, G. F. and Lorinez, A. T., Virology 171, 306–311 (1989).
7. Cole S. T. and Streeck, R. E., J. Virol. 56, 85–91 (1986).
8. Volpers, C. and Streeck, R. E., Virology 181, 419–423 (1991).
9. Zachow. K. R., Ostrow, R. S. and Faras, A. J., Virology 158, 251–254 (1987).
10. Fuchs, P. G., Iftner, T., Weninger, J., and Pfister, H., J. Virol. 58, 626–634 (1986).
11. Kiyono, T., Adachi, A. and Ishbashi, M., Virology 177, 401–405 (1990).
12. Beaudenon, S., Praetorius, F., Kremsdorf, D., Lutzner, M., Worsaac. N., Pehau-Arnaudet, G. and Orth, G., J. Inves. Dermatol. 88, 130–135 (1987).
13. Beaudenon, S., Kremsdorf, D., Obalek, S., Jablonska, S., Croissant, O., Pehau-Arnaudet, G., and Orth, G., Virology 161., 374–384 (1987).
14. Sanger, F., Nicklen, S. and Coulson, A. R., Natl. Acad. Sci. USA 74, 5463–5467 (1977).
15. Knippers, R. in Curr. Top. Microbiol. Immunol. 144 (Knippers, R. and Levine, A. J., Eds.), 137–142 (1989).
16. Birnstiel, M. L., Busslinger, M. and Strub, K., Cell 41, 349–359 (1985).
17. Weiss, E. A., Gilmartin, G. M. and Nevins, J. R., EMBO J. 10, 215–219 (1991).
18. Gloss, B., Bernard, H. U., Seedorf, K. and Klock, G., EMBO J. 12, 735–3743 (1987).
19. Garcia-Garranca, A., Thierry, F. and Yaniv, M., J. Virol. 62, 4321–4330 (1988).
20. Chong, T., Chan, W. K. and Bernard, H. U., Nucl. Acids Res. 18, 465–470 (1990).
21. Benoist, C. and Chambon, P., Nature 290, 304–310 (1981).
22. Wingender, E., Nucl. Acids Res. 16, 1879–1902 (1988).
23. Gloss, B., Chong, T. and Bernard, H. U., J. Virol. 63, 1142–1152 (1989).
24. Jantzen, H. M., Strähle, U., Gloss, B., Stewart, F., Schmid, W., Boshart, M., Miksicek, R. and Schütz, G., Cell 49, 29–38 (1987).
25. Lamberti, C., Morrissey, L. C., Grossman, S. T. and Androphy, E. J., EMBO J. 9, 1907–1913 (1990).
26. Pecoraro, G., Morgan, D. and Defendi, V., Proc. Natl. Acad. Sci. USA 86, 563–567 (1989).
27. Halbert, C., Demers, G. W. and Galloway, D. A., J. Virol. 65, 473–478 (1991).
28. Storey, A., Pim, D., Murray, Osborn, K. Banks, L. ad Crawford, L., EMBO J. 7, 1815–1820 (1988).
29. Miller, J., McLachlan, A. D. and Klug, A., EMBO J. 4, 1609–1614 (1985).
30. Berg, J. M., Science 232, 485–487 (1986).
31. Storey, A., Almond, N., Osborn, K. and Crawford, L., J. Gen. Virol. 71, 965–970 (1990).
32. Schneider-Gädicke, A. and Schwarz, E., EMBO J. 5, 2285–2292 (1986).
33. Seedorf, K., Oltersdorf, T., Krämmer, G. and R öwekamp, W., EMBO J. 6, 139–144 (1987).
34. Smotkin, D. and Wettstein, F. O., Proc. Natl. Acad. Sci. USA 83, 4630–4684 (1986).
35. Phelps W. C., Yee. C. L., Müger, K. and Howley, P. M., Cell 53, 539–547 (1988).
36. Münger, K., Weness, B. A., Dyson, N., Phelps, W. C., Harlow, E. and Howley, P. M., EMBO J. 8, 4099–4105 (1989).
37. Figge, J. and Smith, T. F., Nature 334. 109 (1988).
38. Needlenman, S. B. and Wunsch, C. D., J. Mol. Biol. 48, 443–450 (1970)
39. Kootsky, L. A., Galloway, D. A. and Holmes, K. K., Am. J. Epidemiol. Rev. 10, 122–163 (1988).

We claim:

1. Purified DNA derived from Human Papillomavirus 42 selected from the group consisting of:

(a) the nucleotide sequence shown in FIG. 1 (SEQ ID NO: 1); and (b) a nucleic acid sequence fully complementary to SEQ ID NO: 1.

2. A purified DNA selected from the group consisting of:

(a) a sequence consisting of nucleotide 476 to nucleotide 820 as set forth in FIG. 1 (SEQ ID NO: 1);

(b) a sequence consisting of nucleotide 542 to nucleotide 820 as set forth in FIG. 1 (SEQ ID NO: 1);

(c) a sequence fully complementary to the sequence set forth in (a); and (d) a sequence fully complementary to the sequence set forth in (b).

3. A purified DNA selected from the group consisting of:

(a) a sequence consisting of nucleotide 108 to nucleotide 563 as set forth in FIG. 1 (SEQ ID NO: 1);

(b) a sequence consisting of nucleotide 114 to nucleotide 563 as set forth in FIG. 1 (SEQ ID NO: 1);

(c) a sequence fully complementary to the sequence set forth in (a); and (d) a sequence fully complementary to the sequence set in (b).

4. A purified DNA selected from the group consisting of:
(a) a sequence consisting of nucleotide 724 to nucleotide as set forth in FIG. 1 (SEQ ID NO: 1);
(b) a sequence consisting of nucleotide 829 to nucleotide as set forth in FIG. 1 (SEQ ID NO: 1);
(c) a sequence fully complementary to the sequence set in (a); and
(d) a sequence fully complementary to the sequence set in (b).

5. A purified DNA selected from the group consisting of:
(a) a sequence consisting of nucleotide 2672 to nucleotide as set forth in FIG. 1 (SEQ ID NO: 1);
(b) a sequence consisting of nucleotide 2702 to nucleotide as set forth in FIG. 1 (SEQ ID NO: 1);
(c) a sequence fully complementary to the sequence set in (a); and
(d) a sequence fully complementary to the sequence set in (b).

6. A purified DNA selected from the group consisting of:
(a) a sequence consisting of nucleotide 3282 to nucleotide as set forth in FIG. 1 (SEQ ID NO: 1); and
(b) a sequence fully complementary to the sequence set forth in (a).

7. A purified DNA selected from the group consisting of:
(a) a sequence consisting of nucleotide 3919 to nucleotide 4203 as set forth in FIG. 1 (SEQ ID NO: 1); and
(b) a sequence fully complementary to the sequence set forth in (a).

8. A purified DNA selected from the group consisting of:
(a) a sequence consisting of nucleotide 4348 to nucleotide 5853 as set forth in FIG. 1 (SEQ ID NO: 1);
(b) a sequence consisting of nucleotide 4423 to nucleotide 5853 as set forth in FIG. 1 (SEQ ID NO: 1);
(c) a sequence fully complementary to the sequence set forth in (a); and
(d) a sequence fully complementary to the sequence set forth in (b).

9. A purified DNA selected from the group consisting of:
(a) a sequence consisting of nucleotide 5756 to nucleotide 7342 as set forth in FIG. 1 (SEQ ID NO: 1);
(b) a sequence consisting of nucleotide 5837 to nucleotide 7342 as set forth in FIG. 1 (SEQ ID NO: 1);
(c) a sequence fully complementary to the sequence set forth in (a); and
(d) a sequence fully complementary to the sequence set forth in (b).

* * * * *

UNITED STATES PATENT AND TRADEMARK OFFICE
CERTIFICATE OF CORRECTION

PATENT NO.:    5,952,487

DATED:         September 14, 1999

INVENTOR(S):   Wolfgang PHILIPP et al.

It is certified that several errors appear in the above-identified patent and that said Letters Patent is hereby corrected as shown below:

Claim 3, col. 17, line 1, "set in" should read --set forth in--.

Claim 4, col. 17, lines 4 and 6, second occurrence of "nucleotide" should read --nucleotide 2757--;

lines 9 and 11, "set in" should read --set forth in--.

Claim 5, col. 17, lines 14 and 16, second occurrence of "nucleotide" should read --nucleotide 1895--;

lines 19 and 21, "set in" should read --set forth in--.

Claim 6, col. 17, line 24, second occurrence of "nucleotide" should read --nucleotide 3641--.

Signed and Sealed this

Twenty-fifth Day of April, 2000

Attest:

Q. TODD DICKINSON

*Attesting Officer*    *Director of Patents and Trademarks*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 7917 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

```
CTTATTATAA ACTACAATCC TGGCTTTGAA AAATAAGGGA GTAACCGAAT TCGGTTCAAC      60

CGAAACCGGT ACATATATAA ACCACCCAAA GTAGTGGTCC CAGTTAAGGC AGAATGTCAG     120

GTACATCTGC CTCATCACAG CCACGCACAT TATACCAATT GTGTAAGGAA TTTGGGCTGA     180

CATTGCGGAA TTTACAGATT TCCTGCATTT GGTGCAAAAA GCACTTAACA GGCGCAGAGG     240

TGCTCGCGTA CCATTTTAAA GATTTGGTAG TGGTGTGGAG GAAGGACTTT CCATATGCTG     300

CATGTGCATT TTGTTTAGAA TTTAATTCTA AAATTTGTGC ACTGCGACAC TACGAAAGAT     360

CAGCATTTTG GTATACAGTG GAGAAAGAAA CTGGACTACT TTTAGAAGAA CAACAAATTA     420

GATGTGCCTT GTGTCAAAAG CCGTTATCAC AGAGCGAAAA AAACCATCAT ATTGATACAG     480

GTACAAGATT TCAATTTATA TTGTGTCAGT GGACGGGTCG GTGTACGCAT TGCAGAGGAC     540

AATGCGTGGA GAGACGCCTA CCCTAAAGGA CATTGTTTTG TTTGACATAC CAACGTGTGA     600

GACACCCATT GACCTGTATT GCTATGAACA ATTGGACAGC TCAGATGAAG ATGACCAAGC     660

CAAACAGGAC ATACAGCGTT ACAGAATACT GTGTGTGTGT ACACAGTGTT ACAAGTCTGT     720

TAAACTCGTT GTGCAGTGTA CAGAGGCGGA CATAAGAAAC CTGCAACAGA TGCTTTTGGG     780

CACACTGGAT ATTGTGTGTC CTTTGTGTGC CCGCGTGGAG TAACTGCAAT GGCGGATGAT     840

ACAGGTACAG AGGAGGGGCT AGGGTGTTCT GGATGGTTTT GTGTAGAAGC TATAGTAGAC     900

AAAACAACAG AAAATGCTAT TTCAGATGAC GAGGACGAAA ATGTAGACGA TAGTGGGTTA     960

GATCTTGTGG ATTTTGTAGA TAATAGTACA GTAATACATA CAAAGCAGGT ACATGCACAA    1020

GCCTTATTAA ATAAACAACA AGCACATGCA GATCAGGAGG CAGTACAGGC ACTAAAACGA    1080

AAGCTATTAG GCAGTCCATA TGAAAGCCCT GTCAGTGATT CACAGCACAG CATAGACAAC    1140

GAACTAAGTC CTAGGCTTGG CGGTTTAACG CTATGTCGGG GGTCCAAGG GGCCAAACGA     1200

CGATTATTCC AGTCACTGGA AAATCGAGAC AGTGGATATG GCTATTCTGA AGTGGAAGTA    1260

CAGCAGACAC AGGTAGAACA CGGACATGGC GCCGTACATG GACTATGGG TAACGGGGGG     1320

GCAGTGGGTA GTGAACTTGG GGTGCAGGAA AATGAAGAAG GTAGTACTAC AAGTACGCCT    1380

ACAACAAGGG TGGTAGAATT ACTTAAGTGT AAGAACCTGC ATGCAACATT GTTAGGTAAG    1440

TTTAAAGAAT TGTTTGGAGT GTCATTTGGC GATTTAGTAA GACAGTTTAA AAGTGACAAA    1500

AGCAGTTGTA CAGACTGGGT TATTGCAGCA TTTGGGGTTA ATCATAGTAT TGCAGAAGGG    1560

TTTAATACAT TAATTAAAGC AGATTCACTA TATACACATA TACAATGGCT AACCTGTACG    1620

TGGGGCATGG TGTTATTAAT GCTAATTAGA TTTAAATGTG GAAAAAATCG TACTACAGTG    1680

TCCAAAGGCC TTAGTAAATT ATTAAACATA CCTACAAATC AATTATTAAT AGAGCCACCT    1740

CGGTTACAAA GTGTGGCTGC CGCCATATAC TGGTTTAGAT CAGGAATATC TAATGCTAGC    1800
```

| | |
|---|---|
| ATTGTAACCG GAGACACACC AGAGTGGATT CAAAGACAAA CAATTTTAGA ACATTGTTTT | 1860 |
| GCAGATGCCC AATTTAATTT AACAGAAATG GTGCAATGGG CATATGATAA TGATATTACT | 1920 |
| GAAGACAGTG ACATTGCATA TGAATATGCA CAACGGGCAG ACAGGGATAG CAATGCTGCT | 1980 |
| GCATTTTTAA AAAGTAACTG CCAGGCAAAA TATGTAAAAG ATTGTGGCGT CATGTGCAGA | 2040 |
| CATTATAAAA AAGCACAAAT GAGACGTATG TCTATGGGTG CATGGATAAA ACATAGAAGT | 2100 |
| GCCAAGATAG GGGATAGTGG AGATTGGAAA CCTATAGTAA AATTTATTAG ATATCAACAA | 2160 |
| ATTGATTTTT TAGCATTTAT GTCTGCATTT AAAAAGTTTT TACATAATAT ACCTAAAAAA | 2220 |
| AGTTGTTTAG TGTTAATTGG TCCTCCAAAT ACAGGAAAAT CACAGTTTGG AATGAGTTTA | 2280 |
| ATAAACTTCT TAGCAGGAAC TGTAATATCA TTTGTAAATT CACATAGCCA TTTTTGGCTG | 2340 |
| CAGCCATTGG ACAGTGCAAA AATAGCTATG CTGGATGATG CAACTCCACC ATGTTGGACA | 2400 |
| TATTTAGATA TATATTTAAG AAATTTATTA GATGGCAATC CATGCAGTAT AGATAGAAAA | 2460 |
| CATAAAGCAT TAACAGTTGT TAAGTGCCCA CCATTACTTA TAACATCAAA TACAGATATT | 2520 |
| AGAACAAATG ACAAATGGAA ATACCTATAC AGCAGAGTTA GTTTATTTGA ATTTCCAAAT | 2580 |
| CCATTTCCAT TAGATACAAA TGGAAATCCT GTATATGAAT TAAATGACAA AAATTGGAAA | 2640 |
| TCATTTTTTC AAAGGTTGTG GTCCAGCTTA GAATTTCAAG AATCAGAGGA CGAGGAAGAC | 2700 |
| TATGGAGAGA CTGGCCAAAC GTTTAGATGC GTGCCAGGAA CAGTTGTTAG AACTGTATGA | 2760 |
| GGAAAATAGT AGGGATTTAC AAAAACATAT TGAACATTGG AAATGTTTAC GTATGGAGGC | 2820 |
| AGTGGTATTG TATAAGGCCC GTGAAATGGG CTTTGCAAAT ATAGGACATC AAATAGTACC | 2880 |
| AACATTGGAA ACATGTAGAG CCAAGGCCCA CATGGCAATT GAAATACACT TGGCATTAGA | 2940 |
| GACATTATTG CAGTCCTCGT ATGGTAAAGA ACCATGGACA TTGCAAGAAA CAAGTAATGA | 3000 |
| ACTGTGGCTT ACGAATCCTA AAAAATGTTT TAAAAAACAA GGACGTACCG TGGAGGTTAT | 3060 |
| ATTTGATGGA AAACAGGACA ATGCAATGCA TTATACAGCA TGGACATATA TATATATACA | 3120 |
| AACTGTGCAA GGTACATGGT GTAAAGTACA AGGACACGTT TGCCATGCAG GACTATATTA | 3180 |
| TATTGTGGAA AATATGAAAC AGTTTTATTG TAATTTTAAA GAGGAGGCAA AAAAATATGG | 3240 |
| GGTAACAGAC CAATGGGAGG TACATGATGG CAATCAGGTG ATTGTTTCTC CTGCACCCAT | 3300 |
| ATCTAGCACC ACATCCACCG ACGCAGAGAT ACCCTCTACT GGATCTACTA AGTTGGTACA | 3360 |
| ACAAGTGTGC ACCACAAACC CATTGCACAC CACAACGTCC ATTGACAACC ACCACGCAGA | 3420 |
| CTGTACAGAC GGAACAGCAT ACAACGTGCC CATCCAAACC TCACCGCCAC GAAAACGATA | 3480 |
| CAGACAGTGT GGACAGTCGC CATCACAGCA CCTGCAGCAC TCAAACCCCA GCATCCCCAG | 3540 |
| CATCCCCAGC GCATCCGTGG ACCCTGGATT GTGTGGGGTC AGAACTAACA GTGAAAACTG | 3600 |
| TAACAAGCGA CGGAACCACT GTGGAAGTCA GGCTACGCCT GTAATTCATT TACAAGGTGA | 3660 |
| CCCTAATTGC CTAAAATGCC TACGATTTAG GCTAAAAAGA AATTGTTCAC ATTTATTTAC | 3720 |
| ACAGGTGTCA TCTACATGGC ATTTAACAGA AAATGATTGT ACACGTGACA CTAAAACTGG | 3780 |
| TATAATAACA ATACATTATT ATGATGAAGC ACAAAGAAAT TTATTTTTAA ATACTGTAAA | 3840 |
| AATACCTTCT GGGATAAAAT CCTGTATTGG ATATATGTCT ATGTTACAGT TTATATGATT | 3900 |
| AGTTGTATAT GTGTATAAAC AGTTATAGGA CTTCAATACT GTGACTCCAC AACGTGTGGG | 3960 |
| ACAACCGGCC AGAAACTGCT GCTTTTATTG TTTATAGTTG TTGGTGCGTG TGTTGTGTGT | 4020 |
| GTGTGGATTA GTTTACAAAA TTATCCATAT CCTGTATGGG CCTCTTGCCT TGCTAGCTAC | 4080 |
| CTAACATTGG TGCTATTATC ATGGTTGCAG GTACTAACAT ACTTTGACTA TTTTTTTCTA | 4140 |
| TGTTTAATCA TTCTTGGTAT TCCTTCTGTC TTACTAACAT TACTAATACA TTTAGCAATA | 4200 |

```
CAATAACACA TATTAGTTTA GGTGTGTGTG TGTGGTGTGC ATGTGATTTG TACATGGTTG    4260

TACATATATA ATACCAATTA TTGTTTGGCT ACTATTTTCA TTTATAGCCA CACTGCTGTT    4320

TTGCATATTG GTATTACAAA CATATAAACT GTTACCATAC GTATATACAG TGCTGTAAAT    4380

AAACTTTTGT TATATTGTGT GTACTTCTTT TGTGCTATTA CAATGCCACC ACAACGGTCC    4440

CGCAGACGAA AGCGGGCCTC TGCCACACAA TTATATCAAA CGTGTAAGGC CTCAGGGACA    4500

TGTCCTCCAG ATGTTATTCC CAAAGTTGAA GGAACCACAT TGGCAGATAA AATTTTACAA    4560

TGGGGTAGTT TAGGCGTGTT TTTTGGGGGG TTGGGAATTG GCACTGGTGC AGGTACGGGT    4620

GGGCGCACGG GCTATGTGCC TCTGGGAACA AGGCCTCCTG TAATTGCTGA ACCAGGACCT    4680

GCAGTACGCC CACCAATAGC TGTTGACACC GTGGGCCAT CTGATCCTTC TATTGTTTCC    4740

TTATTAGAAG AGTCATCAGT TATTGATGCA GGAATAACAG TACCTGATAT TACTTCTCAT    4800

GGAGGTTTTA ATATTACTAC ATCTACTGGT GGGCCTGCCT CAACGCCTGC TATATTAGAT    4860

ATCTCCCCTC CCACTAATAC TATACGTGTC ACAACAACTA CATCTACCAA TCCTTTATAT    4920

ATTGATCCTT TTACATTGCA GCCGCCATTG CCAGCAGAGG TTAATGGGCG CCTATTAATA    4980

TCTACTCCTA CCATCACACC CCACTCATAT GAAGAAATAC CAATGGACAC GTTTGTTGTA    5040

TCTACAGATA CAACTAACAC ATTTACTAGT ACTCCCATTC CTGGCCCTCG GTCGTCTGCA    5100

CGCCTGGGGT TATATTCTAG AGCAACGCAA CAACGTCCAG TTACTACCAG TGCATTTTTA    5160

ACATCTCCTG CACGGTTGGT TACTTATGAC AATCCAGCCT ATGAAGGACT TACGGAGGAT    5220

ACATTAGTAT TTGAACATCC ATCCATTCAT ACTGCACCTG ACCCTGATTT CATGGATATA    5280

GTTGCATTGC ATCGTCCTAT GTTATCATCC AAACAGGGTA GTGTACGTGT TAGTAGAATT    5340

GGACAAAGGC TGTCTATGCA GACACGTCGC GGGACCCGTT TTGGGTCACG TGTACACTTT    5400

TTTCATGACC TTAGCCCTAT TACACACTCT TCAGAAACTA TTGAATTACA GCCTTTATCT    5460

GCTTCTTCAG TATCTGCAGC CTCCAATATT AATGATGGGT TATTTGATAT TTATGTTGAT    5520

ACTAGTGATG TAAATGTTAC AAATACCACT TCCTCTATAC CTATGCATGG TTTTGCTACC    5580

CCCCGTTTGT CCACTACATC TTTCCCTACA TTACCTAGCA TGTCTACACA TTCTGCCAAT    5640

ACCACCATAC CTTTTTCGTT TCCTGCCACT GTGCATGTGG GCCCTGATTT ATCTGTTGTG    5700

GACCACCCAT GGGACAGTAC CCCAACGTCT GTAATGCCTC AGGGTAACTT TGTAATGGTA    5760

TCAGGATGGG ATTTTATATT GCATCCTAGT TATTTTTGGC GTAGGCGCCG TAAACCTGTA    5820

CCATATTTTT TTGCAGATGT CCGTGTGGCG GCCTAGTGAC AACAAGGTTT ATCTACCTCC    5880

TCCTCCTGTT TCCAAGGTGG TCAGCACTGA TGAATATGTG CAACGCACCA ACTACTTTTA    5940

CCATGCCAGC AGTTCTAGGC TATTGGTTGT TGGTCACCCT TATTACTCTA TTACAAAAAG    6000

GCCAAATAAG ACATCTATCC CCAAAGTGTC TGGTTTACAG TACAGAGTAT TTAGAGTTAG    6060

GCTCCCTGAT CCTAATAAGT TTACATTGCC TGAAACTAAT TTATATAACC CAGAGACACA    6120

GCGCATGGTG TGGGCCTGTG TGGGGCTAGA AGTAGGTCGT GGACAGCCTT TGGGCGTTGG    6180

TATTAGTGGC CATCCATTAT TGAATAAGTT GGATGATACT GAAAATGCGC CTACATATGG    6240

TGGAGGCCCT GGTACAGACA ATAGGGAAAA TGTTTCTATG GATTATAAAC AAACACAGTT    6300

GTGTTTAGTT GGCTGTAAAC CTGCCATAGG GGAGCACTGG GGTAAAGGTA CTGCCTGTAC    6360

ACCACAGTCC AATGGTGACT GCCCACCATT AGAATTAAAA AATAGTTTTA TTCAGGATGG    6420

GGATATGGTG GATGTAGGGT TTGGGGCACT AGATTTTGGT GCTTTACAAT CCTCCAAAGC    6480

TGAGGTACCT TTGGATATTG TAAATTCAAT TACTAAATAT CCTGATTACT TAAAAATGTC    6540

TGCTGAGGCC TATGGTGACA GTATGTTTTT CTTTTTAAGG CGAGAACAAA TGTTTGTTCG    6600
```

```
TCATTTGTTT AATAGGGCTG GCGCAATTGG TGAACCTGTA CCTGATGAAC TGTATACCAA    6660

GGCTGCTAAT AATGCATCTG GCAGACATAA TTTAGGTAGT AGTATTTATT ATCCTACCCC    6720

TAGTGGTTCT ATGGTAACAT CTGATGCACA ACTATTTAAT AAACCATATT GGTTACAACA    6780

AGCACAAGGA CACAATAATG GTATATGTTG GGGAAATCAG CTATTTTTAA CTGTGGTTGA    6840

TACTACCCGT AGTACTAACA TGACTTTGTG TGCCACTGCA ACATCTGGTG ATACATATAC    6900

AGCTGCTAAT TTTAAGGAAT ATTTAAGACA TGCTGAAGAA TATGATGTGC AATTTATATT    6960

TCAATTGTGT AAAATAACAT TAACTGTTGA AGTTATGTCA TATATACACA ATATGAATCC    7020

TAACATATTA GAGGAGTGGA ATGTTGGTGT TGCACCACCA CCTTCAGGAA CTTTAGAAGA    7080

TAGTTATAGG TATGTACAAT CAGAAGCTAT TCGCTGTCAG GCTAAGGTAA CAACGCCAGA    7140

AAAAAAGGAT CCTTATTCAG ACTTTTGGTT TTGGGAGGTA AATTTATCTG AAAAGTTTTC    7200

TACTGATTTA GATCAATTTC CTTTAGGTAG AAAGTTTTTA CTGCAGGCCG GGTTGCGTGC    7260

AAGGCCTAAA CTGTCTGTAG GTAAACGAAA GGCGTCTACA GCTAAATCTG TTTCTTCAGC    7320

TAAACGTAAG AAAACACACA AATAGATGTA TGTAGTAATG TTATGATACA TATTTATGTT    7380

ATTTATTTGT GTACTGTGTT AATAAACTAC TTTTTATATG TTGTGTGTTC TCCATTTTGT    7440

TTTTTGTACT CCATTTTGTT TCTAGACCGA TTTCGGTTGT ATCTGGCCTG TTACCAGGTG    7500

CATTGGCCAT GTTTCCTAAC ATTTTGCAAA CCTATTCACT TTTTAAATTT ATAAATGCAA    7560

TATGTGCTGC CAACTGTTTT ATGGCACGTA TGTTCTGCCA ACGTACACTC CCTAATTCCT    7620

TTACATAACA CACACGCCTT TGCACAGGCA TGTGCACAAA GGTTGGCAAA GGTTAGCATA    7680

TCTCTGCAGT TACCCATTTC CTTTTTCCTT TTTTTTATGT ATGAGTAACT TAATTGTTAT    7740

ATGTAATAAA AAAGCTTTTA GGCACATATT TTCAGTGTTG GCATACACAT TTACAAGTTA    7800

CCTTGGCTTA AACAAGTAAA GTTATTTGTC ACTGTTGACA CATTACTCAT ATATATAATT    7860

TGTTTTTAAC ATGCAGGTGG CAACCGAAAC CGGTACATAA ATCCTTCTTA TTCTTTT       7917

(2) INFORMATION FOR SEQ ID NO:2:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: misc_feature
          (B) LOCATION: 5..8
          (D) OTHER INFORMATION: /note= "N = unknown."

(xi) SEQUENCE DESCRIPTION: SEQ ID NO:2:

ACCGNNNNCG GT                                                          12
```